United States Patent [19]

Kanda

[11] Patent Number: 5,178,141
[45] Date of Patent: Jan. 12, 1993

[54] LIVER FUNCTION TESTING APPARATUS

[75] Inventor: Masahiko Kanda, Osaka, Japan

[73] Assignee: Sumitomo Electric Industries, Ltd., Osaka, Japan

[21] Appl. No.: 526,885

[22] Filed: May 21, 1990

[30] Foreign Application Priority Data

May 24, 1989 [JP] Japan .................. 1-132345

[51] Int. Cl.$^5$ ............................................. A61B 5/00
[52] U.S. Cl. .................. 128/633; 128/666; 356/41
[58] Field of Search .............. 128/633, 634, 664–666; 356/41

[56] References Cited

U.S. PATENT DOCUMENTS

| 3,677,648 | 7/1972 | Dorsch | 356/40 |
| 4,017,192 | 4/1977 | Rosenthal | 356/201 |
| 4,602,641 | 7/1986 | Feinberg | 128/653 AF |
| 4,905,703 | 3/1990 | Kanda et al. | 128/666 |

Primary Examiner—Lee S. Cohen
Assistant Examiner—Robert L. Nasser, Jr.
Attorney, Agent, or Firm—W. G. Fasse; D. H. Kane, Jr.

[57] ABSTRACT

In a liver function testing apparatus, light sources (11, 12) expose vital tissue (15) to first light of a wavelength absorbed by the specific dye dosed into blood of the vital tissue to be taken in and removed by the liver and second light of a wavelength not absorbed by the dye. Optical pulses passing through the vital tissue are received by a light receiving element (13) and first and second outputs from element (13) are sampled by an A-D converter (30) to produce respective digital signals. Pulsation components of the outputs of the receiving light are detected by high-pass filters (51, 52) and amplifiers (53, 54). A coefficient of a linear regression expression between intensity values of the pulsation components and an average value using the sampled first and second outputs of the received light are determined for performing a biocalibration. A value correlated with a specific dye concentration in the blood is calculated based on sampling outputs during a prescribed period and based on the determined average value after injection of the specific dye. Thus, a coefficient of a simulation function as a time function, is obtained by using the method of least squares and a blood plasma disappearance rate and a retention rate are obtained on the basis of the coefficient of the simulation.

22 Claims, 10 Drawing Sheets

VITAL TISSUE

TIME (SEC)

Y = .869716 r = .999

| | |
|---|---|
| T1 | 8a1 |
| T2 | 8a2 |
| TMAX | 8b1 |
| TMIN | 8b2 |
| m | |
| i1 | 8c1 |
| i2 | 8c2 |
| CT1(1) | 8d1 |
| ( | ( |
| CT1(n) | 8dn |
| ITM | 8i1 |
| TIM1 | 8i2 |
| TIM2 | 8i3 |
| K | 8j1 |
| R | 8j2 |
| r2 | 8j3 |
| CT2(1) | 8e1 |
| ( | ( |
| CT2(n) | 8en |
| A | 8f1 |
| S0' | 8f2 |
| r1 | 8f3 |
| CT1 0 | 8f4 |
| Cg(1) | 8g1 |
| ( | ( |
| Cg(m) | 8gm |

FIG.9

```
* * * * * * * * * * *
* ICG MONITOR CALIBRATION *
* * * * * * * * * * *

PLEASE ATTACH THE SENSOR
```

FIG.10

```
PLEASE PREPARE THE ICG INJECTION

OK  →  START
```

FIG.11

```
       1→2→3→4→5 sec
```

LIVER FUNCTION TESTING APPARATUS

CROSS-REFERENCE TO RELATED APPLICATIONS AND PATENTS

The present invention relates to the following U.S. patents and patent applications:
1) U.S. Pat. No. 4,905,703, issued: Mar. 6, 1990, Inventor: Masahiko Kanda et al., entitled: LIVER FUNCTION TESTING APPARATUS.
2) U.S. Pat. No. 5,054,915, issued: Oct. 8, 1991, Inventor: Masahiko Kanda et al., Title: LIVER FUNCTION TESTING APPARATUS.
3) U.S. Pat. No. 5,054,916, issued: Oct. 8, 1991, Inventor: Masahiko Kanda et al., Title: LIVER FUNCTION TESTING APPARATUS.
4) U.S. patent application No. 07/800,865, filed Nov. 26, 1991, Inventor: Masahiko Kanda, Title: LIVER FUNCTION TESTING APPARATUS.

FIELD OF THE INVENTION

The present invention relates to a liver function testing apparatus. More specifically, it relates to a liver function testing apparatus for automatically performing tests for measuring and diagnosing a liver function by injecting a specific dye, which is selectively taken in and removed only by the liver, into the patient's blood to calculate a value which represents a concentration of the specific dye in the blood.

BACKGROUND INFORMATION

In general, the blood plasma disappearance rate and the retention rate for testing and diagnosing of a liver function have been measured by a method of blood collection using indocyanine green (hereinafter referred to as ICG) as a specific dye.

According to the ICG method, an intravenous injection of ICG is applied to a testee and blood is collected three times after lapses of five, ten and fifteen minutes from the injection, and blood serum is separated upon coagulation of a blood clot so that absorbance at a wavelength of 805 nm is measured through a spectrophotometer to obtain ICG concentration values in the blood serum for each of the lapsed time intervals of five, ten and fifteen minutes relative to a previously obtained calibration curve (corresponding ICG concentration in blood vs absorbance), thereby to calculate the blood plasma disappearance rate and the retention rate. Japanese Patent Publication No. 60-58649 proposes a method of measuring the blood plasma disappearance rate and the retention rate without performing blood collections. According to said method, light is applied through the body surface of an organism, which in turn transmits light of a wavelength having a high ICG absorption sensitivity and light of a wavelength having substantially no ICG absorption sensitivity. The respective quantities of transmitted light are measured to obtain the blood plasma disappearance rate and the retention rate based on changes of the light quantities with time (dye disappearance curve).

Japanese Patent Laying-Open No. 64-17630 discloses an apparatus in which light is applied through the body surface of an organism and the absorbance of ICG is measured to obtain the blood plasma disappearance rate and the retention rate based on changes of the measured absorbance (dye disappearance curve). In said apparatus, a calibration is performed before measurements are made so that changes in the blood quantities in the organism, can be canceled out or disregarded.

In the conventional method of blood collection, it is necessary to correctly measure the times when blood collections are made after injection. However, under actual test conditions it is difficult to accurately measure the time and the operation for such measurement is complicated. Further, the testee is subjected to mental and physical burdens by the blood collection. In addition, the index $R_{MAX}$ measuring method for ascertaining the blood plasma disappearance rate repeatedly by changing the quantity of ICG injection is often used these days but said method requires several blood collections and the burdens on the testee are further increased.

According to the measuring method without blood collection as disclosed in Japanese Patent Publication No. 60-58649 mentioned above, or Japanese Patent Laying-Open No. 61-162934, the output of a sensor actually attached to an organism fluctuates in response to an influence such as blood flow disturbances caused by compression of a blood vessel, vibration of the organism subjected to the measurement, pulsation in the organism, changes in the blood volume in the vital tissue, for example, the blood volume being changed by mere vertical movement of an arm etc. Such influences make it difficult to obtain a correct dye disappearance curve.

Consequently, the blood plasma disappearance rate and the retention rate obtained by the dye disappearance curve cannot be said to be correct.

The above mentioned apparatus disclosed in Japanese Patent Laying-Open No. 64-17630 requires a calibration before any measurements can be made. Therefore, the operation is complicated. In addition, changes in the blood volume in the vital tissue can be compensated for to some extent but not in a satisfactory manner because the calibration is preferably performed immediately before an injection of a specific dye but since it takes time in reality before the injection of the specific dye becomes effective, the calibration does not effectively contribute to increasing the measurement precision.

SUMMARY OF THE INVENTION

Therefore, it is a principal object of the present invention to provide a liver function testing apparatus which can effectively remove adverse influences such as a blood flow disturbance, a vibration or pulsation in an organism, and a change of the blood volume in the vital tissue, when a sensor is attached to the organism and which thus enables a correct measurement.

Briefly stated, in the apparatus of the present invention, the vital tissue is exposed to a first light of a wavelength absorbed by the specific dye which is dosed into the blood of the vital tissue, to be taken in and removed by the liver and a second light of a wavelength not absorbed by the dye. First and second photoelectric conversion signals corresponding to the first light and to the second light obtained from the vital tissue, are sampled and only pulsation components are detected. A coefficient of a linear regression expression between the pulsation components of the first and second photoelectric conversion signals immediately before the injection of the specific dye and a base value using the sampled first and second photoelectric conversion signals, are determined. A value correlated with the specific dye concentration in the blood, is calculated based on a sampling signal during a prescribed lapse of time from the injection of the specific dye and based on said determined coefficient and on said base value.

Therefore, according to the present invention, there is no necessity of collecting blood and the testee needs only to endure the injection of the specific dye, which makes it possible to considerably reduce the mental and physical burdens on the testee. Furthermore, it is now possible to remove said adverse influences such as a blood flow disturbance, and a vibration or pulsation in an organism to which a sensor is attached.

In a preferred embodiment of the present invention, first and second photoelectric conversion signals are detected several times and if the intensities of pulsation components of the detected first and second photoelectric conversion signals are represented as $T_{1P}$ and $T_{2P}$, a linear regression analysis is performed according to the following equation:

$$\log T_{1P} = A \cdot \log T_{2P},$$

whereby a constant A is obtained. If the sampled first and second photoelectric conversion signals are represented as $T_{1C}$ and $T_{2C}$, an average value $So'$ of said conversion signals is obtained by the equation:

$$So' = \frac{\sum_{i=1}^{n} (\log T_{1C}(i) - \log T_{2C}(i))}{n},$$

wherein n is the number of samples taken, as described below.

At the same time, the maximum value of the first photoelectric conversion signal $T_{1C}$ sampled several times is obtained as $T_{10}$.

According to another preferred embodiment of the invention, if the values of the sampled first and second photoelectric conversion signals are represented as $T_1$ and $T_2$, the value Sg correlated with the specific dye concentration, is calculated by the below indicated equation based on said constant A, on said average value $So'$, and on said maximum value $T_{10}$ obtained as described above.

$$Sg = \frac{\log T_{10}[\log T_1 - A \cdot \log T_2 - So']}{2 \log T_{10} - A \cdot \log T_2 - So'}.$$

In this preferred embodiment of the invention, the blood plasma disappearance rate of the specific dye or simultaneously the retention rate of the specific dye during a prescribed period of time, can be obtained based on a calculated coefficient of a simulation function.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 8A to 8C are flow charts for explaining a specified operation of the embodiment of the present invention, in which FIG. 8A shows a data sampling subroutine, FIG. 8B shows a calibration mode, and FIG. 8C shows a measurement mode.

FIGS. 9 to 12 illustrate exemplary displays on a display device as shown in FIG. 5.

DESCRIPTION OF THE PREFERRED EMBODIMENTS AND OF THE BEST MODE OF THE INVENTION

Figure 1:
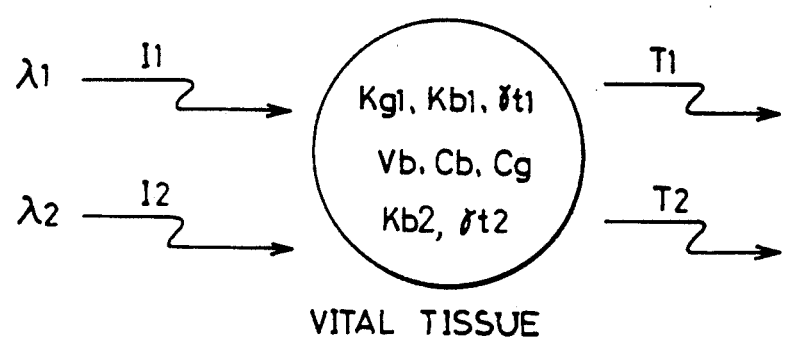
FIGS. 1 to 4 are diagrams for explaining the principle of the present invention.

FIGS. 1 to 4 are diagrams for illustrating the principle of biocalibration in the present invention.

In the following description, symbol $I_1$ indicates quantities of light having a wavelength $\lambda_1$ which is largely absorbed by the specific dye and $I_2$ indicates light of a wavelength $\lambda_2$ which is not absorbed by the specific dye incident upon vital tissue. Symbols $T_1$ and $T_2$ indicate light quantities after passage through a prescribed optical path in the vital tissue. Relations between the incident light quantities $I_1$ and $I_2$ and the passing light quantities $T_1$ and $T_2$ following an injection of the specific dye, are as follows:

$$\log I_1/T_1 = Kg_1 \cdot Cg \cdot Vb + f_1(Cb, Vb) + \gamma t_1 \quad (1)$$

$$\log I_2/T_2 = f_2(Cb, Vb) + \gamma t_2 \quad (2)$$

where $Kg_1$ represents an absorption coefficient of the specific dye at wavelength $\lambda_1$; $\gamma t_2$ represents an absorbance by the tissue at wavelength $\lambda_2$; Vb represents a blood volume in the sample; Cb represents a blood concentration in the sample; and Cg represents a specific dye concentration. Symbols $f_1$ and $f_2$ represent functions which are determined by characteristics of the blood at the wavelengths $\lambda_1$ and $\lambda_2$.

On the other hand, relations between the incident light quantities $I_1$ and $I_2$ and the passing light quantities $T_1$ and $T_2$ before injection of the specific dye are as follows:

$$\log I_1/T_1 = f_1(Cb, Vb) + \gamma t_1 \quad (3)$$

$$\log I_2/T_2 = f_2(Cb, Vb) + \gamma t_2 \quad (4)$$

If only the pulsation components of the passing light quantities $T_1$ and $T_2$ are detected, the above indicated equations (3) and (4) are modified as follows:

$$\Delta \log I_1/T_1 = f_1(Cb, \Delta Vb)$$

$$\Delta \log I_2/T_2 = f_2(Cb, \Delta Vb)$$

Figure 2:
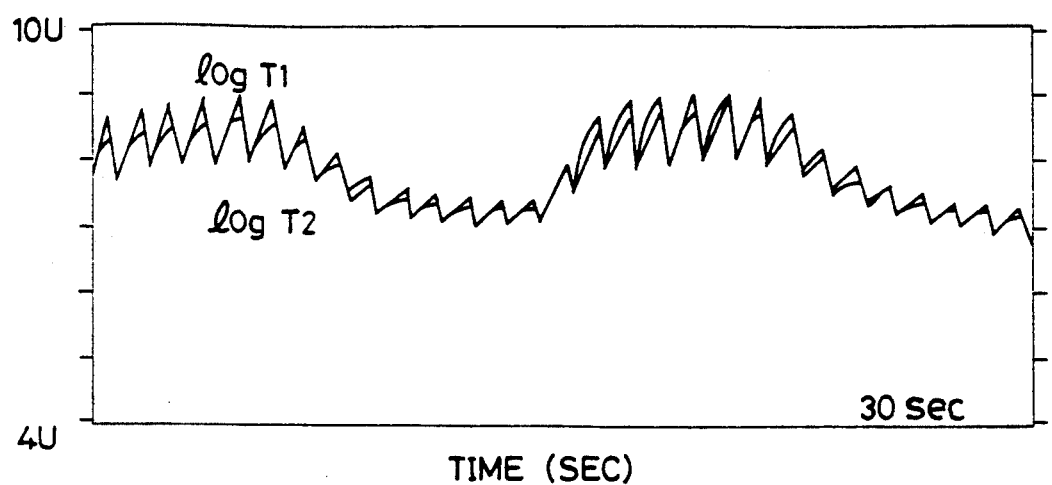
Figure 3:
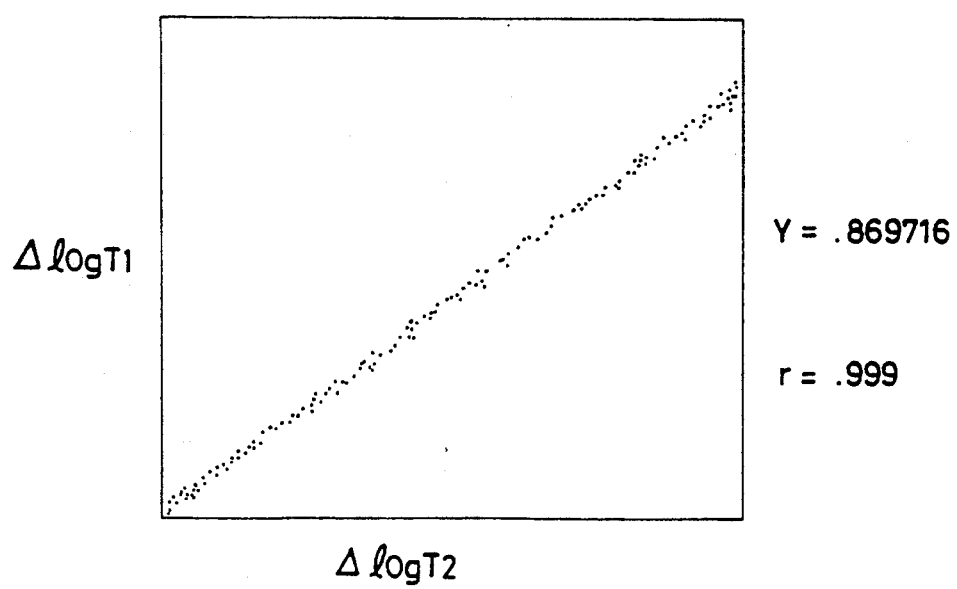

This relationship is measured as shown in FIG. 2 and corresponds to the linear relationship shown in FIG. 3. These data are obtained by attaching a sensor to an organism and fluctuating the blood volume in the organism. It has been confirmed that such linearity is reproducible with no individual differences. Therefore, the expressions (3) and (4) would appear as follows:

$$\Delta \log T_1 = A \cdot \Delta \log T_2 \quad (5)$$

Thus, it is expressed as follows:

$$\log I_1 - f_1(Cb, \Delta Vb) = A[\log I_2 - f_2(Cb, \Delta Vb)] \quad (6)$$

Since the main component changing in the expressions (3) and (4) before injection of the specific dye, is the blood, the expression (6) can be represented as follows:

$$\log I_1 - f_1(Cb, Vb) - \gamma t_1 = A[\log I_2 - f_1(Cb, Vb) - \gamma t_2] \quad (6)'$$

Then, by using the expressions (1) and (2) after injection of the specific dye to obtain $$S' = \log T_1 - A \log T_2 \quad (7),$$

the following expression is obtained:

$$S' = \log I_1 - Kg \cdot Cg \cdot Vb - f_1(Cb, Vb) - \gamma t_1 - \quad (8)$$
$$A[\log I_2 - f_2 - f_2(Cb, Vb) - t_2]$$

If the expression (6) is used in the above indicated expression (8), the following expression is obtained:

$$S' = -Kg \cdot Cg \cdot Vb + \gamma t_1 + \gamma t_2 \quad (9)$$

In addition, if the average value So' before injection of the specific dye is represented as: $So' = \gamma t_1 - \gamma t_2$ and a relationship of $S' - So'$ is set, the function S is expressed as follows:

$$S = -Kg \cdot Cg \cdot Vb$$

Therefore, it is understood that a signal of the function S can be obtained by using the diagram of FIG. 3 as a biocalibration curve.

Although the absorption coefficient Kg is constant, the function S permits assuming that the blood volume Vb changes from time to time, and an accurate value of the specific dye concentration cannot be obtained, because the value of Cg is influenced by the blood volume Vb in the organism.

Figure 4:
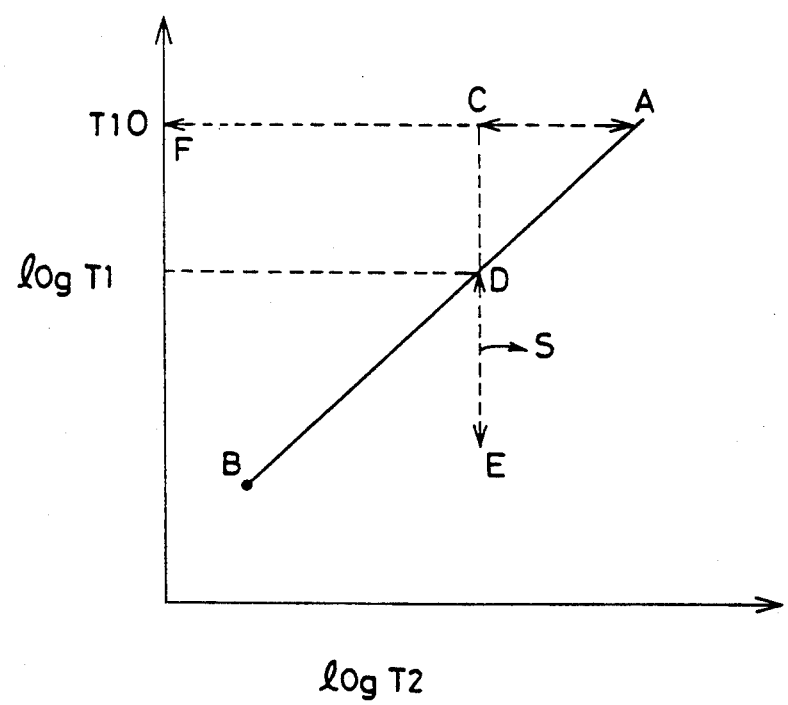

Referring to FIG. 4, $\overline{AB}$ represents a calibration curve. When the specific dye is injected, only the signal of $\log T_1$ fluctuates, to reach a point E, for example. At this time, $\overline{DE}$ which is the value of the function S after a lapse of $t_1$ minutes, becomes the function S as shown in the expression (9). The blood volume Vb in the expression (9) can be interpreted as $\overline{CD}$, and hence, normalizing the Y coordinate of a point A as $T_{10}$, the same is expressed as follows:

$$Vb \propto 1 + \frac{\log T_{10} - (A \cdot \log T_2 + S6)}{\log T_{10}} \quad (10)$$

Hence, a signal Sg corresponding to the specific dye concentration Cg can be found by the expressions (7) and (10) as follows:

$$Sg = \frac{\log T_1 - A \cdot \log T_2 - So'}{1 + \frac{\log T_{10} - A \cdot \log T_2 - So'}{\log T_{10}}}$$
$$= \frac{\log T_{10}[\log T_1 - A \cdot \log T_2 - So']}{2 \log T_{10} - A \cdot \log T_2 - So'}$$

Kg1: ABSORPTION COEFFICIENT OF SPECIFIC DYE (WAVELENGTH: λ1)
Kb1: ABSORPTION COEFFICIENT OF BLOOD AT WAVELENGTH λ1
Kb2: ABSORPTION COEFFICIENT OF BLOOD AT WAVELENGTH λ2
γt1: ABSORBANCE OF TISSUE AT WAVELENGTH λ1
γt2: ABSORBANCE OF TISSUE AT WAVELENGTH λ2
Vb: BLOOD VOLUME IN SAMPLE
Cb: BLOOD CONCENTRATION IN SAMPLE
Cg: SPECIFIC DYE CONCENTRATION IN SAMPLE.

Figure 5:
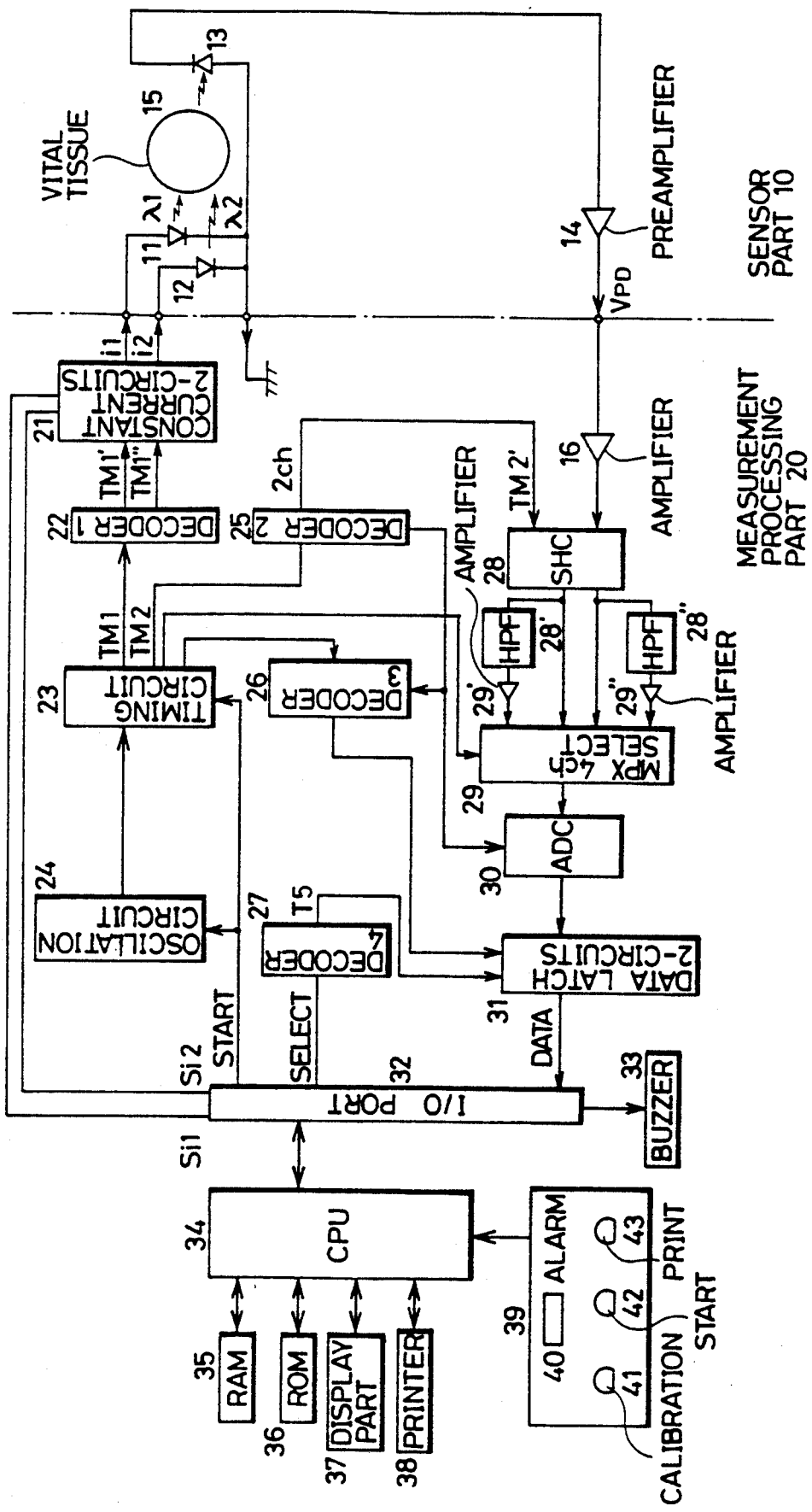
FIG. 5 is a schematic block diagram showing an embodiment of the apparatus of the present invention.

FIG. 5 is a schematic block diagram showing an embodiment of the present invention.

Referring to FIG. 5, a liver function testing apparatus comprises a sensor section 10 and a measurement processing section 20. The sensor section 10 includes a first light source 11, a second light source 12, a light receiving element 13 and a preamplifier 14.

The first light source 11 generates optical pulses of a wavelength $\lambda_1$ having a large absorbance by the specific dye. The light source 12 provides optical pulses of a wavelength $\lambda_2$ having no absorbance by the dye. The light receiving element 13 receives light that has passed through the vital tissue 15 from the light sources 11 and 12 thereby passing through a prescribed optical path. The light sources 11 and 12 are driven by the measurement processing section 20 to alternately emit light in a pulse mode operation, respectively.

The measurement processing section 20 includes a CPU 34 which operates as arithmetic device. The CPU 34 supplies a start signal to an oscillation circuit 24 and to a timing circuit 23 through an I/O port 32. The oscillation circuit 24 oscillates at a constant frequency to produce a prescribed clock signal.

Figures 6, 7:
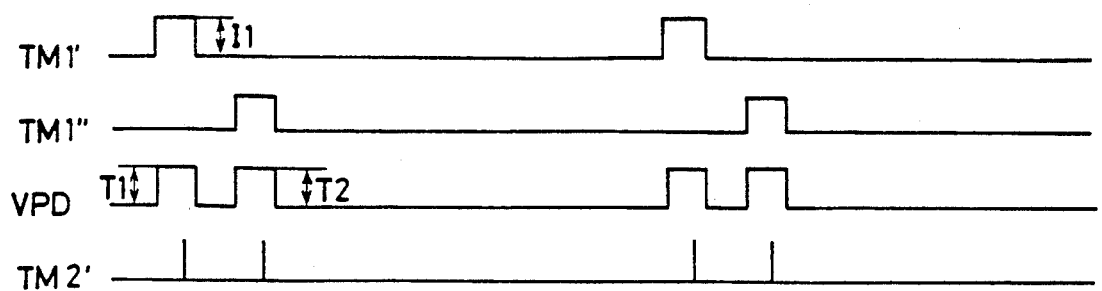
FIG. 6 is a timing chart for detecting light quantities of wavelengths $\lambda_1$ and $\lambda_2$ after passage through a prescribed optical path in a tested object.
FIG. 7 is a diagram showing data stored in a RAM as shown in FIG. 5.

This clock signal and the aforementioned start signal are utilized to supply constant currents $i_1$ and $i_2$ to the first light source 11 and to the second light source 12 from a constant current circuit 21 through the timing circuit 23 and a decoder 22 at timings $TM_1'$ and $TM_1''$ in FIG. 6. The light emitted from the first light source 11 and the light emitted from the second light source 12 pass through the prescribed optical path in the vital tissue 15. The light exiting from the tissue 15 is incident on the light receiving element 13. A current generated by the light receiving element 13 is supplied to the preamplifier 14 and it is subjected to current-to-voltage conversion, while being amplified.

An output signal of the preamplifier 14 is amplified to a level within a prescribed range by an amplifier 16 provided in the measurement processing section 20, whereby an output such as $V_{PD}$ in FIG. 6 is obtained. A sample-and-hold circuit 28 samples and holds the output at timing $TM_2'$, shown in FIG. 6, generated by the timing circuit 23 and a decoder 25.

The signal thus sampled and held is selected by a multiplexer 29 with voltages $T_1$ and $T_2$ shown in FIG. 6 being maintained and the selected signal is converted into a digital signal by an A-D converter 30, to be latched by a data latch 31. During operation, the multiplexer 29, the A-D converter 30, and the data latch 31 are time controlled by the timing circuit 23 and the decoder 26.

The latched data are timed by a decoder 27 by a select signal outputted from the CPU 34 through the I/O port 32, to be stored in a RAM 35 as digital signals $T_1$ and $T_2$. The I/O port 32 is connected with a buzzer 33, which provides a timing buzz for injecting the specific dye. Further, the CPU 34 is connected with the RAM 35, a ROM 36, a display device 37 and a data output such as a printer 38. A slow component is removed from the sampled and held signal by using a high-bandpass filter HPF and an amplifier as shown in FIG. 5, whereby only the pulsation component is taken out. This operation is performed for both $T_1$ and $T_2$ and the respective outputs are amplified by the amplifier 16 and stored in the RAM 35 as digital signals as described above, by means of the multiplexer 29.

Figure 8A:
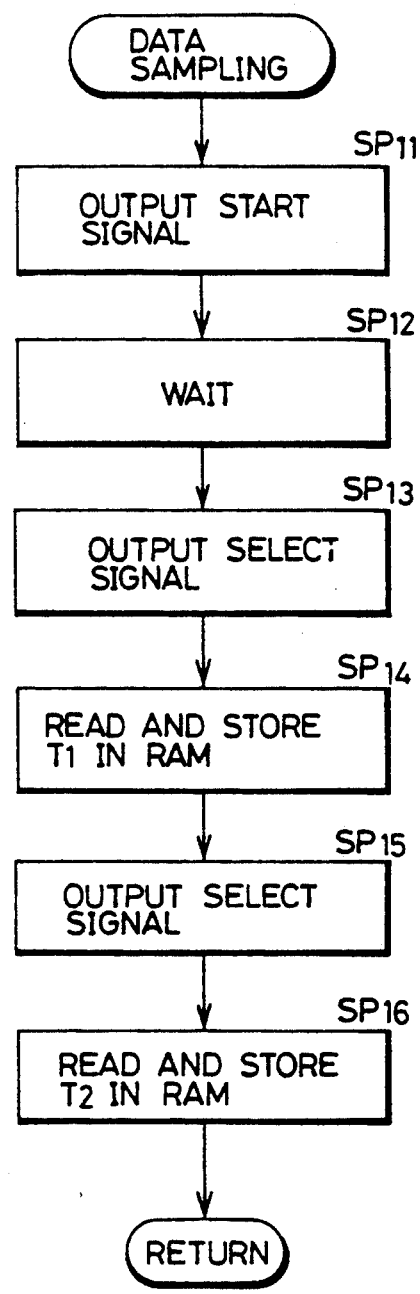
Figure 8B:
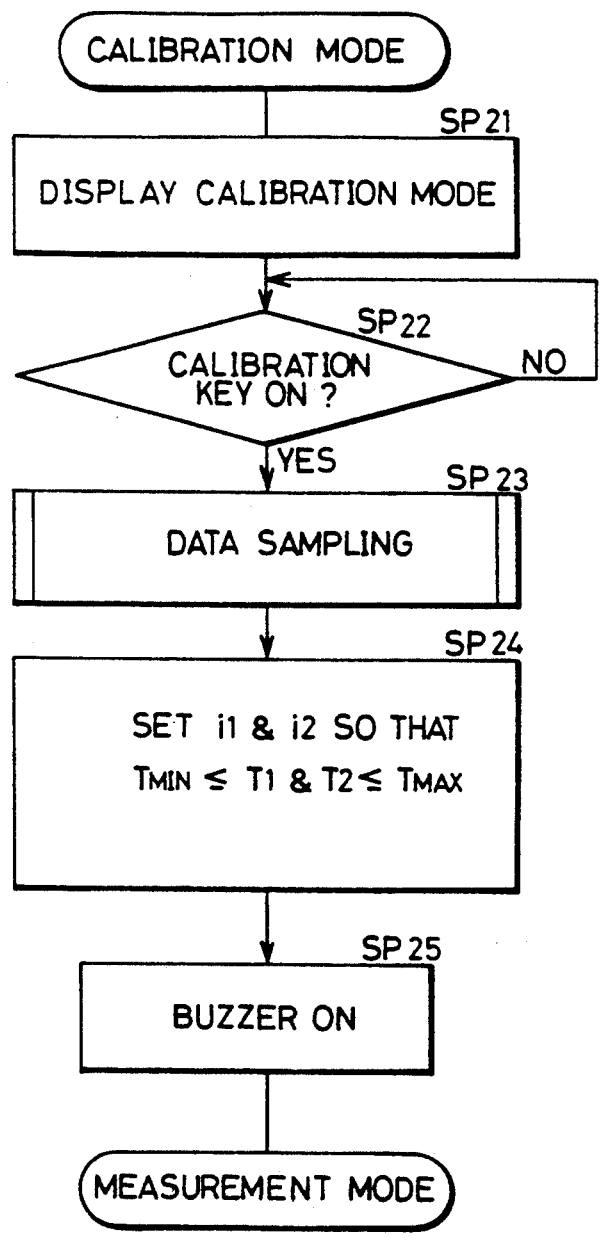
Figure 8C:
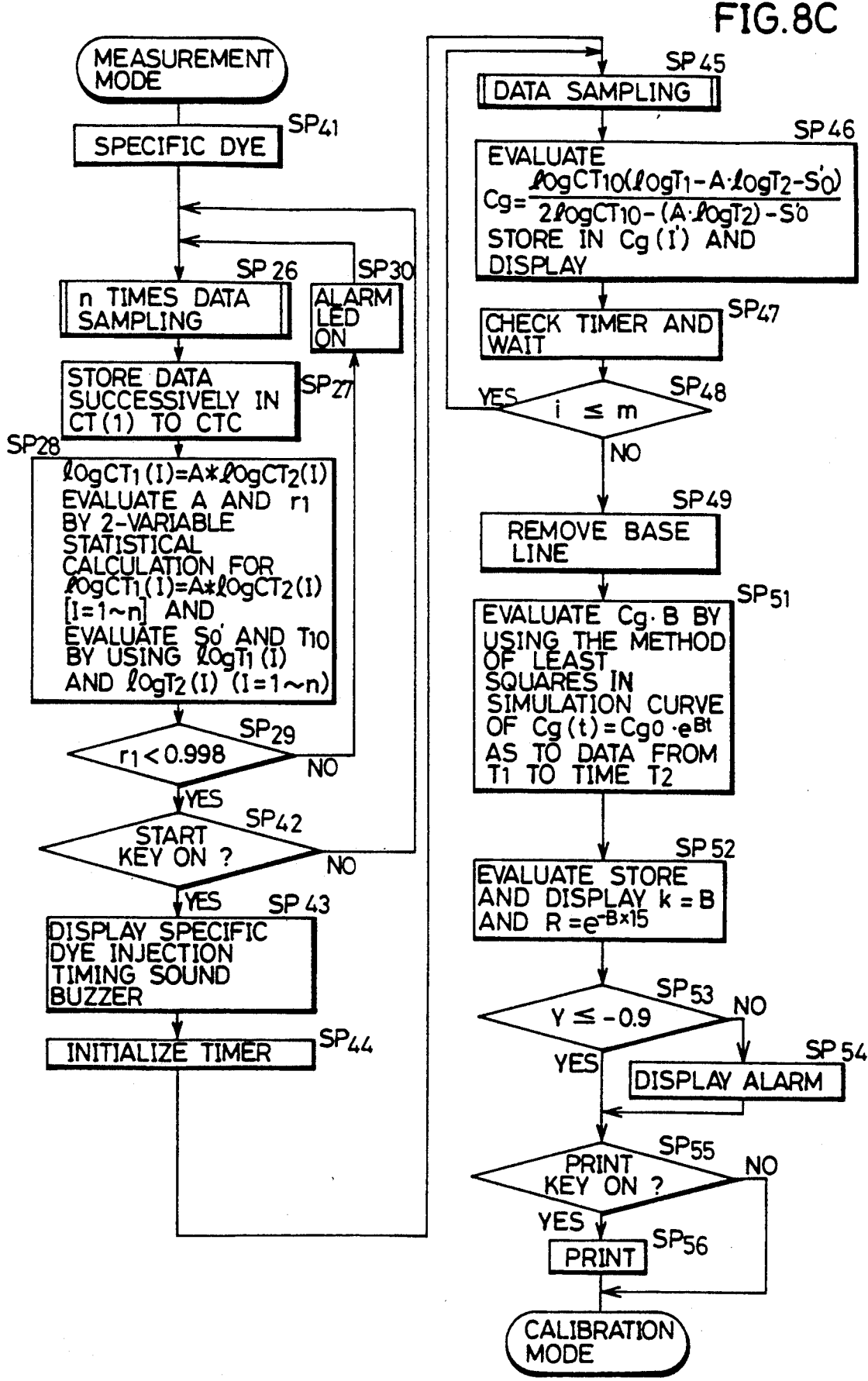

The RAM 35 stores data as shown in FIG. 7 as hereinafter described, and the ROM 36 stores programs based on flow charts as shown in FIGS. 8A to 8C as hereinafter described. The display device 37 displays data as shown in FIGS. 9 to 12, as hereinafter described. The printer 38 provides a printout of the result of a liver function test.

A function section 39 includes an alarm LED 40, a calibration key 41, a start key 42 and a print key 43. The alarm LED 40 displays an alarm when the reliability of the test result is small. The calibration key 41 is used to set a biocalibration mode. The start key 42 is used to command a start of a measurement mode and the print key 43 is used to command a printout of the test result.

FIG. 7 illustrates data stored in the RAM 35 as shown in FIG. 5 and FIGS. 8A to 8C are flow charts for illustrating an operation of the embodiment of the present invention. FIGS. 9 to 12 are illustrative of exemplary displays on the display part as shown in FIG. 5. With reference to FIGS. 5, 8A to 8C and 13, the operation of the embodiment of the present invention will now be described.

First of all, steps SP11 to SP16 shown in FIG. 8A are employed to sample quantities of light of a pair of wavelengths $\lambda_1$ and $\lambda_2$ after passage through a measured object and to store the same in the RAM 35. More specifically, the SPU 34 outputs the start signal from a line as shown in FIG. 5 through the I/O port 32 in step SP11. The voltages $T_1$ and $T_2$ are latched by the start signal, as hereinabove described. The CPU 34 waits until the data are latched in step SP12.

Then, in step SP13, the CPU 34 outputs the select signal to a select line as shown in FIG. 5 through the I/O port 32, to read the data of $T_1$ through the I/O port 32 in step SP14, thereby to store the same in a storage area 8$a$1 of the RAM 35 as shown in FIG. 6.

Similarly, the CPU 34 stores the data of $T_2$ in a storage area 8$a$2 of the RAM 35 in steps SP15 and SP16.

Upon completion of the aforementioned operation in step SP16, the CPU 34 returns to the original step. This will be described with reference to FIG. 8B showing the biocalibration mode.

The biocalibration mode is started before performing of a measurement mode shown in FIG. 8C as hereinafter described. In step SP21, the CPU 34 displays the biocalibration mode on the display device 37 which indicates that the apparatus enters the biocalibration mode and also indicates that the sensor 10 is to be attached as shown in FIG. 9 for example. In accordance with this indication, an operator attaches the sensor 10 to the object 13 to be tested.

Thereafter, the CPU 34 waits until the calibration key 41 is operated in step SP22. When the calibration key 41 is operated, the CPU 34 advances to step SP23, to execute the data sampling subroutine as shown in FIG. 8A, as hereinabove described.

Then, the CPU 34 controls the constant current circuit 21 by using lines Si1 and Si2 as shown in FIG. 5 so that the data $T_1$ and $T_2$ read in step SP23 are within ranges of light quantity data $T_{MAX}$ and $T_{MIN}$ stored in storage areas 8$b$1 and 8$b$2 of the RAM 35. The CPU 34 then stores set values of currents of the lines Si1 and Si2 in storage areas 8$c$1 and 8$c$2 in the RAM 35. Thereafter the currents of the lines Si1 and Si2 regularly flow to the light sources 11 and 12.

Then, the CPU 34 sounds the buzzer in step SP25, to inform that the proper setting is completed. Then, it proceeds to the measurement mode.

The measurement mode will now be described with reference to FIG. 8C.

Steps SP26 to SP29 in FIG. 8C are shown at a flow chart for performing the above mentioned biocalibration. More specifically, the values of $CT_1$ and $CT_2$ converted as the pulsation signals in steps SP26 and SP27, are sampled n times, so that $CT_1(1)$ to $CT_1(n)$ are stored in the areas 8$d$1 to 8$dn$ of the RAM 35 and $CT_2(1)$ to $CT_2(n)$ are stored in the areas 8$e$1 to 8$en$.

In the subsequent step SP28, the CPU 34 performs a 2-variable statistical calculation with respect to log $CT_1(I)$ and log $CT_2(I)$ ($I = 1$ to n) in the following manner:

$$\log CT_1(I) = A \cdot \log CT_2(I)$$

Then, using the value A thus obtained, a correlation coefficient $r_1$ and the n values of $T_1(I)$ and $T_2(I)$ are calculated at the same time, and the value $S'$ is calculated by the following expression:

$$So' = \frac{\sum_{I=1}^{n} (\log T_1(I) - A \log T_2(I))}{n},$$

whereby the maximum value $T_{10}$ of $T_1(I)$ ($I = 1$ to n) is calculated. The values thus obtained are stored in the areas 8/1, 8/2, 8/3 and 8/4 of the RAM 35. Then, in step SP29, the CPU 34 determines whether the correlation coefficient $r_1$ is at least 0.998 in order to varify the reliability of the biocalibration. If it is less than 0.998, the CPU 34 advances to step SP30 to light the alarm LED 40 and returns to step SP22 to perform again a biocalibration. On the other hand, if the correlation coefficient $r_1$ is 0.998 or more, the CPU 34 proceeds to the measurement mode shown in FIG. 8C. The reference value 0.998 of the correlation coefficient $r_1$ herein employed is a mere example, which is determined by the performance of the entire apparatus. In step SP41, a display for the injection of the specific dye is made on the display device 37.

This display is made for example to indicate the injection of a specific dye, e.g., as ICG. In accordance with the display, the operator prepares for injection of the specific dye into the testee or patient. In step SP42, the CPU 34 waits until the start key 42 is operated. During this waiting, the operation in steps SP26 to SP29, namely, the biocalibration is performed repeatedly and the calibration values (A, So' and $T_{10}$) immediately before depression of the start key 42 are stored in the areas 8/1 to 8/4 in the RAM 35. When the start key 42 is depressed, the calibration data immediately before the depression are employed for the subsequent measurement.

Upon determination that the start key 42 is operated, the CPU 34 displays a timing for the injecting of the specific dye in step SP43 by sounding the buzzer 33.

This is displayed as 1→2→3→4→5 as shown in FIG. 11, for example, so that the operator injects the specific dye upon display of "5". The CPU 34 generates a first sound by the buzzer 33 with the displays of "1", "2", "3" and "4", while generating a different sound from the buzzer 33 upon display of "5".

Upon generation of the sound and display, the operator injects the specific dye. The CPU 34 sets "0" as the initial value of a timer in step SP44.

In step SP45, the CPU 34 executes a data sampling program, which is the subroutine as hereinabove described with reference to FIG. 8A. Then, the sampling data are stored in the areas $8a1$ to $8a2$ of the RAM 35 as $T_1$ to $T_2$, respectively. In step SP46, the CPU 34 performs an operation based on the following operation expression by using the coefficients A, B, and $T_{10}$ stored in the areas $8f1$, $8f2$ and $8f4$ of the RAM 35 in the biocalibration mode as described above with reference to FIG. 8B, to store Cg(I) in an area $8g1$ of the RAM 35:

$$Cg = \frac{\log T_{10}[\log T_1(I) - A \cdot \log T_2(I) - So']}{2 \log CT_{10} - A \cdot \log T_2(I) - So'}$$

Figure 12:
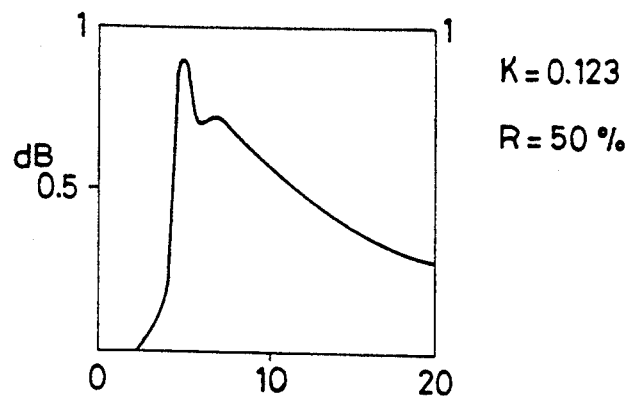

The value of Cg(I) is displayed by the display device 37 in step SP46 in a mode as shown in FIG. 12, for example. Referring to FIG. 12, the abscissa indicates the elapsed time from the injection of the specific dye and the ordinate indicates the value of Cg(I). If m represents the sampling number of a disappearance curve of the specific dye, symbol I indicates integers 1 to m. If $T_s$ represents a measuring time of the disappearance curve, a single sampling time is $ITM = T_s/(m-1)$. The same coincides with the injection time of the specific dye in the case of I = 1. In step SP47 the CPU 34 waits during this sampling ITM.

Figure 13:
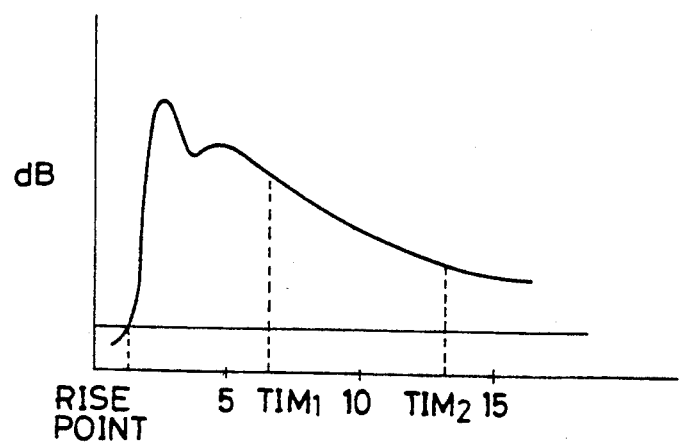
FIG. 13 shows an example of a disappearance curve of a specific dye measured as taught herein.

Upon a lapse of this standby time, the CPU 34 determines whether or not i is greater than m in step SP48. The CPU 34 advances to step SP49 if i is greater than m while the same again returns to step SP45 to repeat sampling if i is less than m. The data Cg(I) stored in the areas $8g1$ to $8gm$ of the RAM 35 draw a disappearance curve of the specific dye as shown in FIG. 13, for example, and the leading edge thereof is detected so that the preceding data are substracted as baselines from the respective values of Cg(I), to be again stored in the areas $8g1$ to $8gm$. $T_1$ to $T_2$ in step SP45 may be average values of k times, in order to improve the accuracy of the measurement.

Then, in step SP51, the CPU 34 finds the constants A and B by using the method of least squares in a simulation curve of $$Cg(t) = Cg0 \cdot e^{B \cdot t}$$
$$t = T_s/(n-1) \text{ (minutes)}$$

with respect to data between times $T_1$ to $T_2$ ($0 < T_1 < T_2 < T_s$) within the data Cg(I) stored in the areas $8g1$ to $8gm$.

Then, the CPU 34 calculates the blood plasma disappearance rate $k = -B$ and the T-minute retention rate $R\% = e^{BT}$ in step SP52, to evaluate k and R which are stored in areas $8f1$ to $8f2$ of the RAM 35, respectively. At this time, the CPU 34 evaluates a correlation coefficient $r_2$ by the method of least squares, and stores the obtained correlation coefficient $r_2$ in a storage area $8f3$ of the RAM 35. The CPU 34 further generates an end sound by the buzzer 33.

Further, the CPU 34 causes the display of the values k and R on the display section 37 in a mode as shown in FIG. 12, for example. Then, in step SP53, the CPU 34 determines whether or not the correlation coefficient $r_2$ is less than $-0.95$, for example. This determination is made to check the degree of correlation since the correlation is improved as the correlation coefficient $r_2$ approaches $-1$. The value $-0.95$ is provisionally selected between zero and $-1$, and the reliability of the apparatus is improved as the value comes closer to $-1$.

If the correlation coefficient $r_2$ is greater than $-0.95$, for example, the CPU 34 determines that the reliability is insufficient and lights the alarm LED 40 in step SP54. On the other hand, if the correlation coefficient $r_2$ is less than $-0.95$, for example, in step SP53, the CPU 34 advances to step SP55 without flashing the alarm LED 281, since the measurement is reliable. In step SP55, the CPU 34 determines whether or not the print key 43 is operated, to cause the printer 38 to print the values k and R % if the determination is: YES.

If necessary, the CPU 34 also causes characteristic dye disappearance curves of Cg(I) stored in the areas $8g1$ to $8gn$ of the RAM 35 to be printed, and to advance to the biocalibration mode as shown in FIG. 8B.

When a determination is made that the print key 43 is not operated in step SP55, the CPU 34 advances to the calibration mode.

By using the value k obtained according to the present invention, the apparatus of the present invention can be used for measuring $R_{MAX}$ by calculating the value k for various amounts of injected ICG.

As described in the foregoing, according to the embodiment of the present invention, vital tissue 15 is exposed to optical pulses of a wavelength considerably absorbed by a specific dye and to optical pulses of a wavelength not absorbed by the dye at prescribed levels and the optical pulses transmitted through a prescribed optical path in the vital tissue are detected so that a biocalibration is performed based on the detection output. By using the coefficient thus obtained, the blood plasma disappearance rate and the retention rate of the specific dye after injection thereof are obtained according to a prescribed calculation expression based on an output of received light in a prescribed period from the injection. Consequently, it is possible to correctly control the time related with the disappearance curve of the specific dye and to obtain correct data.

In addition, the present invention makes it possible to obtain the blood plasma disappearance rate and the retention rate from many data of disappearance curves, not from several samples as in the conventional blood collection method.

In addition, the measurement method can be simplified compared with the conventional testing method in which the quantity of ICG injection is changed and measured several times to obtain the blood plasma disappearance rate and the retention rate.

Furthermore, the present invention makes it possible to remove artifacts such as a blood flow disturbance, vibration and pulsation of an organism, and changes in the blood volume in the organism to which a sensor is attached, which are problems in the prior art. Such removal assures correct measurements. Since calibration is performed immediately before measurement, the precision of measurement is further improved. Accordingly, the apparatus of the present invention can be effectively utilized in the technical fields of measuring a specific dye in vital tissue in a non-invasive manner.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A liver function apparatus for testing the function of a liver, comprising: light source means (11, 12) for exposing vital tissue to first light of a wavelength absorbed by a specific dye dosed into blood of said vital tissue to be taken in and removed by the liver, and to second light of a wavelength not absorbed by said specific dye; photoelectric conversion means (13) for outputting first and second photoelectric conversion signals corresponding to said first light and to said second light applied to said vital tissue by said light source means and obtained from said vital tissue; sampling means (28) for sampling said first and second photoelectric conversion signals from said photoelectric conversion means; said sampling means sampling said first and second photoelectric conversion signals a plurality of times (n), said sampling means further including means for obtaining an average value So' according to the following operation expression:

$$So' = \sum_{i=1}^{n} \frac{(\log T_{1C}(i) - \log T_{2C}(i))}{n}$$

wherein $T_{1C}$ and $T_{2C}$ represent said first and second photoelectric conversion signals sampled n times for obtaining a maximum value $T_{10}$ of said first photoelectric conversion signal; pulsation detecting means (51-54) for detecting only pulsation components of said first and second photoelectric conversion signals from said photoelectric conversion means; decision means (34, SP28) for determining a coefficient of a regression line expression between intensities of said pulsation components of said first and second photoelectric conversion signals obtained from said pulsation detecting means immediately before injection of said specific dye and from said average value So' using said first and second photoelectric conversion signals sampled by said sampling means; and arithmetic means (34) for calculating a value correlated with a specific dye concentration in said blood on the basis of an output of said sampling means during a prescribed period of time following an injection of said specific dye, of said coefficient of said regression line expression, and of said average value So'.

2. The liver function testing apparatus of claim 1, wherein said pulsation detecting means includes means for sampling said first and second photoelectric conversion signals a plurality of times, and wherein said decision means includes means for obtaining a constant A by performing a regression line analysis in accordance with the following operation expression:

$$\log T_{1P} = A \cdot \log T_{2P}$$

wherein $T_{1P}$ and $T_{2P}$ represent average values of said first and second photoelectric conversion signals sampled by said sampling means a plurality of times.

3. The liver function testing apparatus of claim 1, further including coefficient calculating means (34, SP52) for obtaining a coefficient of a simulation function as a function of time by using the method of least squares on the basis of said value correlated with said specific dye concentration obtained by said arithmetic means.

4. The liver function testing apparatus of claim 3, further including means (34, SP52) for obtaining a blood plasma disappearance rate of said specific dye on the basis of said coefficient of said simulation function obtained by said coefficient calculating means.

5. The liver function testing apparatus of claim 4, further including means (37, 38) for outputting said blood plasma disappearance rate obtained by said means for obtaining said blood plasma disappearance rate.

6. The liver function testing apparatus of claim 4, wherein
said means for obtaining said blood plasma disappearance rate includes means for calculating the following operation expression:

$$k = -B$$

where k represents said blood plasma disappearance rate.

7. The liver function testing apparatus of claim 3, further including means (34, SP52) for obtaining a retention rate of said specific dye in said prescribed period of time on the basis of said coefficient of said simulation function obtained by said coefficient calculating means.

8. The liver function testing apparatus of claim 7, further including means (37, 38) for outputting said retention rate.

9. The liver function testing apparatus of claim 7, wherein
said means for obtaining said retention rate includes means for calculating the following operation expression:

$$R \% = e^{Bt}$$

where R % represents said retention rate.

10. The liver function testing apparatus of claim 9, further including informing means (33, SP30) for giving an alarm when said correlation coefficient obtained by said means for calculating said correlation coefficient, is greater than a predetermined value.

11. The liver function testing apparatus of claim 3, wherein
said coefficient calculating means includes means for calculating constants A and B on the basis of the following operation expression:

$$C_g = Ae^{Bt}$$

where t represents said prescribed period of time after injection of said specific dye.

12. The liver function testing apparatus of claim 3, wherein
said coefficient calculating means includes means (SP52) for calculating a correlation coefficient of said simulation function.

13. The liver function testing apparatus of claim 12, further including means (33, SP54) for giving an alarm when said correlation coefficient of said simulation function is greater than a predetermined value.

14. The liver function testing apparatus of claim 1, wherein
said arithmetic means includes means for calculating a value Cg correlated with said specific dye concentration on the basis of said constant A obtained by said obtaining means in accordance with the following operation expression:

$$Cg = \frac{\log T_{10}[\log T_1 - (A \cdot \log T_2 + So')]}{2 \log T_{10} - (A \cdot \log T_2 + So')}$$

where $T_1$ and $T_2$ represent values of said sampled first and second photoelectric conversion signals.

15. The liver function testing apparatus of claim 1, wherein
said decision means includes means (SP28) for calculating a correlation coefficient $r_1$ of said regression line expression.

16. The liver function testing apparatus of claim 1, further including mode selection means (41, 42) for selecting a biocalibration mode for deciding said coefficient of said regression line expression by said decision means, and for selecting a measurement mode for calculating said value correlated with said specific dye concentration by said arithmetic means.

17. The liver function testing apparatus of claim 16, further including means (42) for activating said decision means in response to a selection of said biocalibration mode by said mode selection means.

18. The liver function testing apparatus of claim 16, further including means for activating said arithmetic means in response to a selection of said measurement mode by said mode selection means.

19. The liver function testing apparatus of claim 1, further including setting means (SP241-SP249) for setting intensity levels of said first light and of said second light emitted by said light source means so that levels of said first and second photoelectric conversion signals are within a predetermined range.

20. A lifer function testing apparatus for testing the function of a liver, comprising: light source means for exposing vital tissue to first light of a wavelength absorbed by a specific dye dosed into blood of said vital tissue to be taken in and removed by the liver, and to second light of a wavelength not absorbed by said specific dye; photoelectric conversion means for outputting first and second photoelectric conversion signals corresponding to said first light and to said second light applied to said vital tissue by said light source means and obtained from said vital tissue; sampling means for sampling said first and second photoelectric conversion signals during a prescribed period of time after a lapse of a predetermined time from an injection of said specific dye, said sampling means sampling said first and second photoelectric conversion signals a plurality of times (n), and further including means for obtaining an average value So' according to the following operation expression:

$$So' = \sum_{i=1}^{n} \frac{(\log T_{1C}(i) - \log T_{2C}(i))}{n}$$

wherein $T_{1C}$ and $T_{2C}$ represent said first and second photoelectric conversion signals sampled n times for obtaining a maximum value $T_{10}$ of said first photoelectric conversion signal; arithmetic means for calculating a correlation coefficient correlated with a specific dye concentration in said blood on the basis of values sampled by said sampling means; and means for giving an alarm when said correlation coefficient correlated with specific dye is greater than a predetermined value.

21. A liver function testing apparatus for testing liver function, comprising light source means for exposing vital tissue to first light of a wavelength absorbed by a specific dye dosed into blood of said vital tissue to be taken in and removed by the liver, and to second light of a wavelength not absorbed by said dye; photoelectric conversion means for outputting first and second photoelectric conversion signals corresponding to said first light and to said second light applied to said vital tissue by said light source means and obtained from said vital tissue; indication means for indicating a timing for injecting said specific dye into said blood; sampling means for sampling said first and second photoelectric conversion signals during a prescribed period of time after a lapse of a predetermined time from an indication of said timing for injecting said specific dye by said indication means, said sampling means sampling said first and second photoelectric conversion signals a plurality of times (n), and further including means for obtaining an average value So' according to the following operation expression:

$$So' = \sum_{i=1}^{n} \frac{(\log T_{1C}(i) - \log T_{2C}(i))}{n}$$

wherein $T_{1C}$ and $T_{2C}$ represent said first and second photoelectric conversion signals sampled n times, for obtaining a maximum value $T_{10}$ of said first photoelectric conversion signal; and means for evaluating a specific dye concentration in said blood on the basis of values sampled by said sampling means.

22. A liver function testing apparatus for testing liver function, comprising: light source means for exposing vital tissue to first light of a wavelength absorbed by a specific dye dosed into blood of said vital tissue to be taken in and removed by the liver, and to second light of a wavelength not absorbed by said dye; photoelectric conversion means for outputting first and second photoelectric conversion signals corresponding to said first light and to said second light applied to said vital tissue by said light source means and obtained from said vital tissue; setting means for setting intensity levels of said first light and of said second light emitted from said light source means so that said first and second photoelectric conversion signals are within a predetermined range; sampling means for sampling said first and second photoelectric conversion signals during a prescribed period of time after a lapse of a predetermined time from an injection of said specific dye, said sampling means sampling said first and second photoelectric conversion signals a plurality of times (n), and further including means for obtaining an average value So' according to the following operation expression:

$$So' = \sum_{i=1}^{n} \frac{(\log T_{1C}(i) - \log T_{2C}(i))}{n}$$

wherein $T_{1C}$ and $T_{2C}$ represent said first and second photoelectric conversion signals sampled n times, for obtaining a maximum value $T_{10}$ of said first photoelectric conversion signal; and means for evaluating a specific dye concentration in said blood on the basis of values sampled by said sampling means.

* * * * *